(12) United States Patent
Polanowski

(10) Patent No.: US 7,381,054 B1
(45) Date of Patent: Jun. 3, 2008

(54) DENTURE REMOVER

(76) Inventor: Michiko Taira Polanowski, 219 Harrow Dr., San Antonio, TX (US) 78227

(*) Notice: Subject to any disclaimer, the term of this patent is extended or adjusted under 35 U.S.C. 154(b) by 0 days.

(21) Appl. No.: 11/079,587

(22) Filed: Mar. 14, 2005

Related U.S. Application Data

(60) Provisional application No. 60/552,703, filed on Mar. 12, 2004.

(51) Int. Cl.
*A61C 17/04* (2006.01)
(52) U.S. Cl. .......................... 433/91; 294/64.1
(58) Field of Classification Search ................ 433/91, 433/95, 96, 141, 184–187, 229; 606/107
See application file for complete search history.

(56) References Cited

U.S. PATENT DOCUMENTS

| | | | | |
|---|---|---|---|---|
| 1,400,573 | A * | 12/1921 | Stader | 294/64.1 |
| 2,051,847 | A * | 8/1936 | Halstead | 312/206 |
| 2,177,504 | A * | 10/1939 | Thompson | 206/361 |
| 2,209,424 | A * | 7/1940 | Shipman et al. | 294/64.1 |
| 2,303,393 | A * | 12/1942 | Schmidt | 294/64.1 |
| 2,379,629 | A * | 7/1945 | Eweson | 294/1.2 |
| 2,555,076 | A * | 5/1951 | Crossley | 606/107 |
| 2,607,620 | A * | 8/1952 | Oliveri | 294/64.1 |
| 3,424,486 | A * | 1/1969 | Corley | 294/1.2 |
| 3,644,997 | A | 2/1972 | Fernandez | |
| 4,047,532 | A * | 9/1977 | Phillips et al. | 606/107 |
| 4,274,826 | A | 6/1981 | Huey et al. | |
| 4,377,381 | A | 3/1983 | Westman | |
| 4,593,947 | A * | 6/1986 | Yocum | 294/64.1 |
| 4,822,278 | A * | 4/1989 | Oliva et al. | 433/91 |
| 4,901,606 | A * | 2/1990 | Christensen | 81/57.11 |
| 4,991,570 | A * | 2/1991 | Bullard | 601/164 |
| 5,040,981 | A * | 8/1991 | Oliva | 433/141 |
| 5,106,139 | A * | 4/1992 | Palmer et al. | 294/64.1 |
| 5,256,064 | A * | 10/1993 | Riihimaki et al. | 433/141 |
| 5,306,059 | A * | 4/1994 | Pirrallo | 473/56 |
| 5,525,059 | A * | 6/1996 | Lee | 433/141 |
| 5,622,726 | A * | 4/1997 | Tanner | 425/12 |
| 5,742,971 | A * | 4/1998 | Salinger | 15/167.1 |
| 5,795,001 | A * | 8/1998 | Burke | 294/64.1 |
| 6,039,371 | A * | 3/2000 | Smith | 294/8.6 |
| 6,076,223 | A * | 6/2000 | Dair et al. | 15/167.1 |
| 6,102,203 | A * | 8/2000 | Marro | 206/362.1 |
| 6,170,894 | B1 * | 1/2001 | Baker et al. | 294/64.1 |
| 6,318,685 | B1 * | 11/2001 | Huber | 248/205.5 |
| 6,349,445 | B1 * | 2/2002 | Mackay et al. | 15/167.1 |
| 6,485,281 | B1 * | 11/2002 | Curl | 425/12 |
| 6,709,181 | B1 * | 3/2004 | Montoli | 401/129 |

(Continued)

*Primary Examiner*—Cary E. O'Connor
(74) *Attorney, Agent, or Firm*—Kenneth L Tolar

(57) ABSTRACT

A denture remover includes an elongated, hollow shaft having a lower end and an upper end with an angled portion at the upper end. A suction cup is attached to a distal end of the angled portion. A vacuum release tube extends from the suction cup to an air port within the shaft interior having a spring-biased valve normally positioned therein. A handle is slidably mounted on the shaft and is fastened to the valve. A denture is removed by fastening the suction cup thereto in a conventional fashion. A user simply grasps the handle and pulls the attached denture from the wearer's mouth. To release the denture, a user slides the handle to remove the valve from the port allowing air flow to the suction cup aperture thereby eliminating the vacuum created by the suction cup.

3 Claims, 2 Drawing Sheets

U.S. PATENT DOCUMENTS

| | | | |
|---|---|---|---|
| 7,017,222 B2 * | 3/2006 | Dunn | 15/106 |
| 2002/0100134 A1 * | 8/2002 | Dunn et al. | 15/167.1 |
| 2003/0099918 A1 | 5/2003 | De Luca | |
| 2004/0060577 A1 * | 4/2004 | Dunn | 134/8 |
| 2004/0163979 A1 * | 8/2004 | Bender et al. | 206/361 |
| 2006/0037369 A1 * | 2/2006 | Bright | 70/58 |
| 2006/0037370 A1 * | 2/2006 | Bright | 70/58 |

* cited by examiner

DENTURE REMOVER

CROSS REFERENCE TO RELATED APPLICATIONS

This application is entitled to the benefit of provisional application No. 60/552,703 filed on Mar. 12, 2004.

BACKGROUND OF THE INVENTION

The present invention relates to a device that allows a user to quickly and easily remove, clean and reinstall a denture.

DESCRIPTION OF THE PRIOR ART

Many people, particularly the elderly, wear dentures, which must be periodically removed for cleaning or other maintenance. Typically, the dentures are grasped, manipulated and pulled until properly removed. Such task can be difficult, particularly for the elderly or infirm, or if the denture is adhesively fastened. Furthermore, a denture that is handled in such a fashion can be easily dropped and broken. Accordingly, there is currently a need for a device that allows a user to quickly and conveniently remove a denture for maintenance.

A review of the prior art reveals only one device that assists a user in removing a denture. For example, U.S. published patent application no. 2003/0099918 issued to De Luca discloses a personal denture remover including a loop at one end for insertion of a denture wearer's finger and a hook at another end for attaching to a denture.

U.S. Pat. No. 4,377,381 issued to Westman discloses a denture cleaning tool including a handle having a blade at each of two opposing ends.

U.S. Pat. No. 4,274,826 issued to Huey at al. discloses a denture adjustment tool including a claw having a sharp tip for removing debris from a denture.

U.S. Pat. No. 3,644,997 issued to Fernandez discloses a dental plate having a suction diaphragm for more securely retaining a denture within a wearer's mouth.

Although one denture remover exists in the prior art, it merely includes a hook that is latched to a denture. However, the device includes no means for securing the denture to prevent it from inadvertently releasing during removal. Accordingly, as is the case with removing the denture by hand, the denture can be easily dropped and broken. The present invention addresses this problem by providing a uniquely configured device that can be releasably secured to a denture allowing easy removal thereof. Furthermore, the device includes a gripping means for assuring that the denture does not become detached during removal.

SUMMARY OF THE INVENTION

The present invention relates to a denture remover. The device comprises an elongated, substantially hollow shaft having a lower end and an upper end. At the upper end is an angled portion having a flexible suction cup positioned thereon. The suction cup includes a centrally disposed aperture having a vacuum release tube connected thereto. A distal end of the vacuum release tube is fastened to an air port positioned within the shaft interior. A spring-biased handle is slidably mounted on the shaft and is attached to a valve that is normally positioned within the port to prevent air flow to the vacuum release tube. Accordingly, a user thrusts the suction cup against a denture until it tightly adheres thereto. To release the denture, a user slides the handle to disengage the valve from the air port allowing air flow to the suction cup thereby eliminating the vacuum.

It is therefore an object of the present invention to provide a denture remover that allows a user to quickly and conveniently remove a denture.

It is another object of the present invention to provide a denture remover that eliminates the hazards associated with manually removing a denture.

It is yet another object of the present invention to provide a denture remover that enhances denture hygiene.

Other objects, features, and advantages of the present invention will become readily apparent from the following detailed description of the preferred embodiment when considered with the attached drawings and the appended claims.

DESCRIPTION OF THE PREFERRED EMBODIMENT

Figure 1:
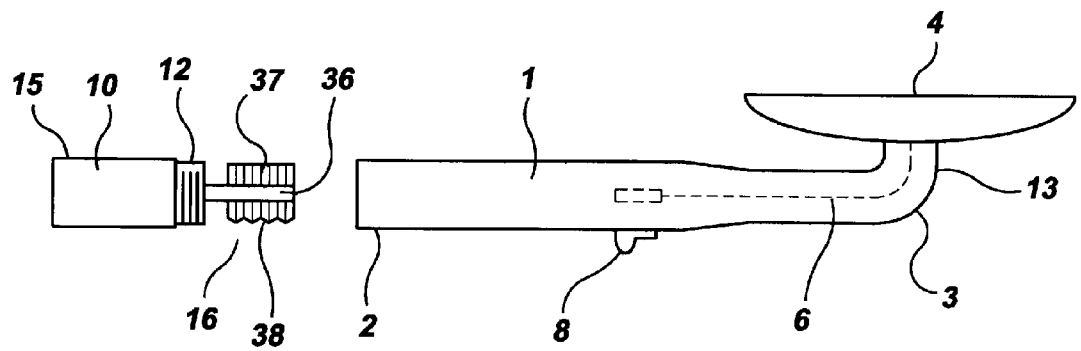
FIG. 1 is a side, partially exploded view of the device.
Figure 2:
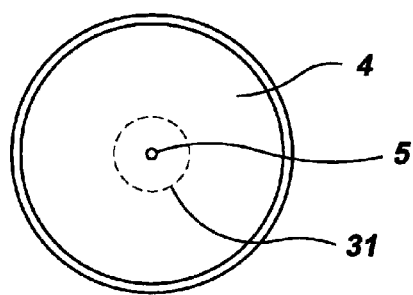
FIG. 2 is a top view of the suction cup according to the present invention.
Figure 3:
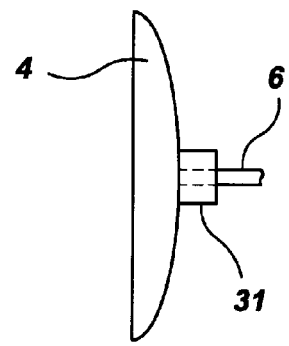
FIG. 3 is a side view of the suction cup.
Figure 4:
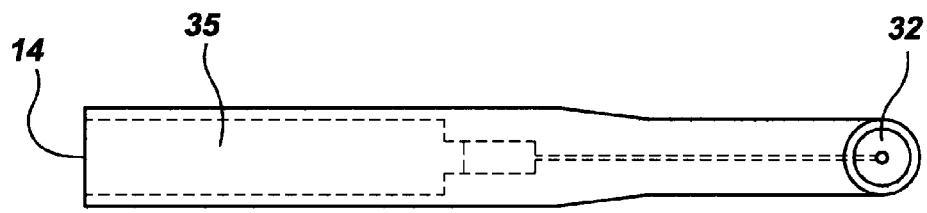
FIG. 4 is a detailed, top view of the shaft.
Figure 5:
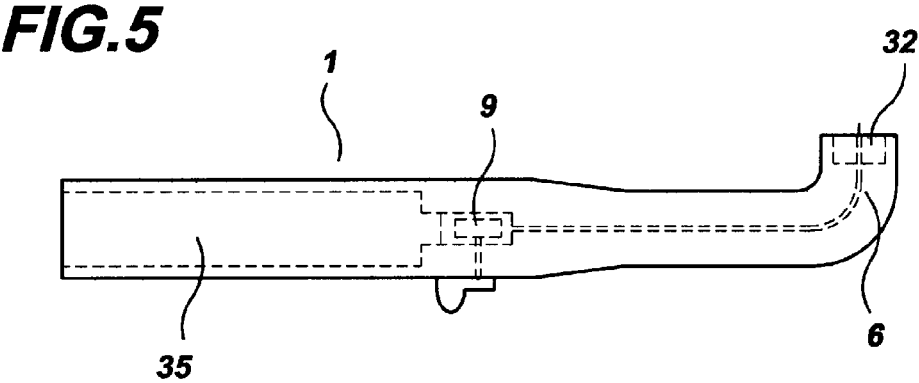
FIG. 5 is a detailed, side view of the shaft.
Figure 6:
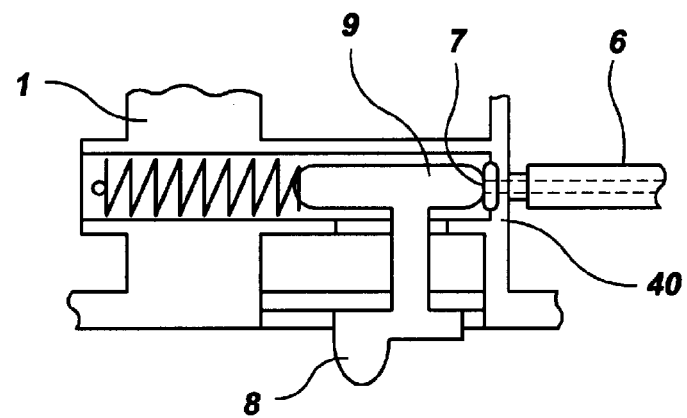
FIG. 6 is a detailed, sectional view of the spring-biased handle and valve mechanism.

Now referring to FIGS. 1-6, the present invention relates to a denture remover for assisting a denture wearer in removing, cleaning and reinstalling a denture. The device comprises an elongated, substantially hollow shaft 1 having a lower end 2 and an upper end 3. At the upper end is an angled portion 13 having a flexible suction cup 4 mounted thereon. Preferably, the suction cup includes a nipple 31 at a lower end that is received within a mating receptacle 32 at the upper end of the handle and which is adhesively bonded therein. The suction cup further includes a centrally disposed aperture 5 having a vacuum release tube 6 connected thereto. A distal end of the vacuum release tube is fastened to an air port 7 positioned within the shaft interior encompassed by an O-ring 40. A spring-biased handle 8 is slidably mounted on the shaft and is attached to a valve 9 that is normally positioned within the port to prevent air flow to the vacuum release tube.

The lower end of the shaft includes a hollow cavity 35 with an internally threaded portion 14 that removably receives a denture brush 15. The denture brush includes a tubular housing 10 with an externally threaded portion 12 on an end thereof for coupling with the internally threaded portion of the cavity. A brush member 16 extends from an end of the housing for cleaning a denture. The brush member includes a spine 36 having rigid bristles 37 on one side thereof and softer, more flexible bristles 38 on an opposing side.

Accordingly, a user thrusts the suction cup against a denture until it tightly adheres thereto. The user then grasps the shaft to remove or install the adhering denture. The angled shaft allows the user to position the cup against an upper or lower denture while the shaft extends horizontally from the wearer's mouth to facilitate proper positioning of the cup. To release the denture, a user slides the handle thereby disengaging the valve from the air port; air can then freely flow to the suction cup thereby eliminating the vacuum.

The above described device is not limited to the exact details of construction and enumeration of parts provided herein. Furthermore, the size, shape and materials of construction can be varied.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A denture remover comprising:

an elongated, substantially hollow shaft having a lower end, an upper end and an interior; said lower end of the shaft including a hollow portion having a denture brush removably received therein, wherein said denture brush includes a tubular housing having an externally threaded portion at an end thereof for coupling with an internally threaded portion on the lower end of the shaft, said denture brush further including a brush member extending from an end of the housing wherein said brush member includes a spine having rigid bristles on a side thereof and flexible bristles on an opposing side;

a flexible suction cup at the upper end of said shaft for removably securing to a denture;

means for selectively releasing said suction cup from a denture when secured thereto wherein said means for releasing said suction cup from a denture when secured thereto includes an aperture disposed on said suction cup, an air port positioned within the shaft, said port in fluid communication with said aperture, a spring-biased handle slidably mounted on said shaft, a valve attached to said handle that is normally positioned within the air port to prevent air flow to the said air port whereby said handle is moved against a bias of said spring to displace said valve from said port allowing air flow to said aperture to eradicate a vacuum created by said suction cup.

2. The denture remover according to claim 1 wherein the upper end of the shaft includes an angled portion to which said suction cup is secured.

3. The denture remover according to claim 2 wherein said suction cup includes a nipple at a lower end that is received within a mating receptacle on said angled portion of said shaft.

* * * * *